(12) United States Patent
Sizer et al.

(10) Patent No.: US 8,685,654 B2
(45) Date of Patent: Apr. 1, 2014

(54) ASSAYS FOR ADSORBED INFLUENZA VACCINES

(75) Inventors: Philip J. Sizer, Frodsham (GB); Jane King-Haughey, Cheshire (GB); David Simpkin, Frodsham (GB); Roger Williams, Liverpool (GB)

(73) Assignee: Novartis AG, Basel (CH)

( * ) Notice: Subject to any disclaimer, the term of this patent is extended or adjusted under 35 U.S.C. 154(b) by 137 days.

(21) Appl. No.: 12/810,307

(22) PCT Filed: Dec. 24, 2008

(86) PCT No.: PCT/GB2008/004286
§ 371 (c)(1),
(2), (4) Date: Sep. 16, 2010

(87) PCT Pub. No.: WO2009/081172
PCT Pub. Date: Jul. 2, 2009

(65) Prior Publication Data
US 2011/0045457 A1 Feb. 24, 2011

Related U.S. Application Data

(60) Provisional application No. 61/008,728, filed on Dec. 24, 2007.

(51) Int. Cl.
*G01N 33/53* (2006.01)
*A61K 39/145* (2006.01)

(52) U.S. Cl.
USPC .................................... 435/7.1; 424/209.1

(58) Field of Classification Search
None
See application file for complete search history.

(56) References Cited

U.S. PATENT DOCUMENTS

| | | | |
|---|---|---|---|
| 4,016,252 A | 4/1977 | Relyveld et al. | |
| 5,443,832 A | 8/1995 | Amerongen et al. | |
| 5,676,976 A | 10/1997 | Lee et al. | |
| 5,851,670 A | 12/1998 | Mitoh et al. | |
| 6,355,271 B1 | 3/2002 | Bell et al. | |
| 6,372,223 B1 | 4/2002 | Kistner et al. | |

FOREIGN PATENT DOCUMENTS

| | | |
|---|---|---|
| WO | WO-93/19780 A1 | 10/1993 |
| WO | WO-96/26741 A1 | 9/1996 |
| WO | WO-97/37000 A1 | 10/1997 |
| WO | WO-00/15251 A2 | 3/2000 |
| WO | WO-00/46147 A2 | 8/2000 |
| WO | WO-01/21151 A1 | 3/2001 |
| WO | WO-01/22992 A2 | 4/2001 |
| WO | WO-01/64846 A1 | 9/2001 |
| WO | WO-02/28422 A2 | 4/2002 |
| WO | WO-02/067983 A1 | 9/2002 |
| WO | WO-02/074336 A2 | 9/2002 |
| WO | WO-02/097072 A2 | 12/2002 |
| WO | WO-03/043415 A1 | 5/2003 |
| WO | WO-03/051394 A2 | 6/2003 |
| WO | WO-03/076601 A1 | 9/2003 |
| WO | WO-2005/033695 A2 | 4/2005 |
| WO | WO-2005/042728 A2 | 5/2005 |
| WO | WO-2005/113756 A1 | 12/2005 |
| WO | WO-2005/113758 A1 | 12/2005 |
| WO | WO-2006/071563 A2 | 7/2006 |
| WO | WO-2007/052060 A1 | 5/2007 |

OTHER PUBLICATIONS

Wood et al. Journal of Biological Standardization, 1977, vol. 5, (3), pp. 237-242.*
Wood et al. Journal of Biological Standardization, 1983, vol. 11 (2), pp. 133-136.*
Adams et al. (Aug. 22, 2005). "An immuno-diffusion assay to assess the protective antigen content of anthrax vaccine," Vaccine 23(36):4517-4520.
Aggerbeck & Heron (1995) Vaccine 13:1360-1365.
Banzhoff (2000) Immunology Letters 71:91-96.
Brands et al. (1999) Dev Biol Stand 98:93-100.
Bresson et al. (2006) Lancet 367:1657-64.
Fitzgerald & Needy (1986) Dev Biol Stand 64:73-79.
Gao et al. (Jan. 2008). "Development of a method for determination of hemagglutinin content in pandemic influenza vaccine containing aluminium adjuvant," Chinese Journal of Biologicals 21(1):60-61, 69.
Gennaro (2000) Remington: The Science and Practice of Pharmacy. 20th edition, ISBN: 0683306472.
Govorkova et al. (2006) J Infect Dis. 194(2):159-67.
Halperin et al. (2002) Vaccine 20:1240-7.
Hehme et al. (2004) Virus Res. 103(1-2):163-71.
Huckriede et al. (2003) Methods Enzymol 373:74-91.
International Search Report mailed Mar. 19, 2009, for PCT Application No. PCT/GB2008/004286 filed Dec. 24, 2008, 3 pages.
Jiang et al. (2004) Vaccine 23:693-698.
Keitel et al. (1996) Clin Diagn Lab Immunol 3:507-510.
Lin et al. (2006) Lancet 368:991-997.
Plotkin & Orenstein, Eds. (2004). Vaccines, 4th edition, ISBN: 0-7216-9688-0.
Powell & Newman, Eds. (1995). Vaccine Design: The Subunit and Adjuvant Approach, ISBN 0-306-44867-X.
Rota et al. (1992) J Gen Virol 73:2737-2742.
Treanor et al. (1996) J Infect Dis 173:1467-1470.
Tree et al. (2001) Vaccine 19:3444-3450.
Williams (1993) Vet Microbiol 37:253-262.
Xing et al. (Sep. 1998). "Single radial immunodiffusion as a method for the assay of the acellular pertussis vaccine components, pertussis toxoid, filamentous haemagglutinin and pertactin," Biologicals 26(3):217-224.
Drescher, J "Comparison of the Adsorption of Influenza Virus Strain B/Berlin/2/55 on Aluminum Oxide and on Aluminum Hydroxide", p. 104-118 for publication Feb. 13, 1961.
Hennessy, A.V., et al, Studies on Vaccination of Infants Against Influenza with Influenza Hemagglutinin (38069) Proceedings of the Society For experimental Biology and Medicine 146, 20-204 (1974).

* cited by examiner

*Primary Examiner* — Bao Li
(74) *Attorney, Agent, or Firm* — Regina Bautista; Otis Littlefield

(57) ABSTRACT

Influenza hemagglutinin (HA) binds to aluminum salt adjuvants and cannot easily be directly assayed directly a single radial immunodiffusion (SRID) test. The invention modifies the SRID protocol for an adsorbed antigen by including a step in which antigen is desorbed prior to diffusion.

22 Claims, No Drawings

ASSAYS FOR ADSORBED INFLUENZA VACCINES

CROSS REFERENCE TO RELATED APPLICATIONS

This is a U.S. National Phase patent application of PCT/GB2008/004286, filed Dec. 24, 2008, which claims priority to U.S. Provisional patent application Ser. No. 61/008,728 filed Dec. 24, 2007, all of which are hereby incorporated by reference in the present disclosure in their entirety.

TECHNICAL FIELD

This invention is in the field of assays performed on influenza vaccines, and in particular vaccines in which antigens are adsorbed onto aluminium salts.

BACKGROUND ART

Various forms of influenza virus vaccine are currently available (e.g. see chapters 17 & 18 of reference 1). Vaccines are generally based either on live virus or on inactivated virus. Inactivated vaccines may be based on whole virions, 'split' virions, or on purified surface antigens.

Current influenza vaccines do not include an adjuvant, except for the FLUAD™ product from Novartis Vaccines, which includes an oil-in-water emulsion. Adjuvants have been used with experimental vaccines, however, with aluminium salts being used on several occasions, particularly for vaccines against pandemic strains. References 2 to 6 use an aluminum hydroxide adjuvant. Reference 7 used a mixture of aluminum hydroxide and aluminum phosphate. Reference 8 also described the use of aluminum salt adjuvants.

The usual assay for standardizing antigen content of influenza vaccines is the single radial immunodiffusion ("SRID") assay [9,10], which was recommended by the WHO in 1978 to replace tests based on agglutination of erythrocytes. The assay is based on diffusion of influenza antigens into agarose gel containing specific anti-hemagglutinin (anti-HA) serum. As antigen diffuses outwards it meets a cognate antibody in the gel and initially forms a visible precipitate as a halo around the well. As diffusion continues, the concentration shifts towards excess substance and the precipitate dissolves. Diffusion continues further until the substance's concentration drops to allow precipitation again. Further diffusion allows precipitation, re-dissolving and re-precipitation until the substance is too low to re-dissolve the rim of the precipitate. The halo then stops increasing in diameter. The diameter of the final halo is directly proportional to the amount of HA antigen in the preparation. By comparing halos produced by an unknown preparation to those of a reference with known HA content, an antigen amount can be assigned to the unknown.

The adjuvanted vaccine in reference 5 was prepared by extemporaneously mixing antigen and adjuvant immediately prior to use. Antigen content had thus been standardized before adjuvant was introduced. If antigen and adjuvant are mixed at the stage of bulk vaccine manufacture, however, the SRID assay will have to be performed on adsorbed antigen. The inventors have found that influenza HA binds to aluminium salt adjuvants so tightly that it does not diffuse well into the SRID gel and so cannot easily be assayed directly by the standard procedure. Thus there is a need to provide improvements to the SRID assay which allow it to be used with pre-adsorbed vaccines.

DISCLOSURE OF THE INVENTION

The invention modifies the influenza SRID assay protocol for an adsorbed antigen by including a step in which antigen is desorbed prior to diffusion. Thus the invention provides a method for performing a SRID assay, comprising the steps of:
(a) obtaining a starting composition comprising an antigen of interest, wherein the antigen is adsorbed to an adjuvant;
(b) treating the starting composition to desorb the antigen from the adjuvant; and
(c) allowing the desorbed composition, or a sample thereof, to diffuse into a gel that contains antibody specific to the antigen of interest.

The invention also provides, in a SKID assay for an adjuvant-adsorbed antigen, the improvement consisting of desorbing the antigen before radial diffusion of the antigen takes place.

More generally, the desorption step can be used prior to any influenza vaccine analytical step with which adsorption will interfere e.g. assay techniques including SDS-PAGE, immunoblotting or western blotting, immunoassays (e.g. ELISA), BCA protein assay, etc. Thus the invention provides a method for performing an assay on an influenza antigen, comprising the steps of
(a) obtaining a starting composition comprising an influenza antigen, wherein the antigen is adsorbed to an adjuvant;
(b) treating the starting composition to desorb the antigen from the adjuvant; and
(c) applying an assay technique to the desorbed composition, or a sample thereof.

The invention also provides, in an assay for an adjuvant-adsorbed influenza antigen, the improvement consisting of desorbing the antigen before assay of the antigen takes place.

The invention also provides an antigen composition that has been assayed by the methods of the invention. The invention also provides a vaccine comprising an antigen that has been assayed by the methods of the invention.

The SRID Assay

The SRID assay of the invention comprises three steps (a) to (c), as described above.

The starting composition to be analysed by the SRID assay includes an antigen which is adsorbed to an adjuvant. The antigen will typically be an influenza virus antigen, as described in more detail below, but SRID assays are also known for use in determining the potency of other vaccines, including inactivated polio and rabies vaccines [9,10]. The antibody included in the gel will be selected according to the antigen being assayed.

The adjuvant to which the antigen is adsorbed will typically be an insoluble metal salt, as described in more detail below.

The SRID assay usually involves introducing a composition to be analysed into a well in a gel. The well is usually circular, and so the diffusion in step (c) will be substantially radial. In the assays of the invention, the adsorbed antigen is desorbed from the adjuvant to allow it to diffuse into the gel. Further details on desorption are given below.

Desorption can take place inside a well of the gel, but will usually take place before an antigen composition is added to a well. Between steps (b) and (c), therefore, the method of the invention may include a step in which the desorbed composition, or a sample thereof, is introduced into a gel that contains antibody specific to the antigen of interest.

A gel used in a typical SRID assay will include multiple wells for receiving samples, permitting parallel analysis. It is normal to test multiple samples of the same material in a single assay, usually at different sample dilutions. The method of the invention may desorb antigens from a single sample and then divide the sample prior to immunodiffusion, in which case desorbed material from step (b) will be split into a number of samples prior to step (c).

The gel used in the SRID assay contains antibody specific to the antigen of interest, at a concentration which permits the formation of immune complexes at a suitable distance from the centre of diffusion for a target antigen concentration. The antibody will be present at a substantially uniform concentration, which may or may not be known. Preparation of such gels is well known in the art for a number of different antigens. Antibody may be monoclonal or polyclonal, but the use of antiserum containing polyclonal antibody is typical. A preferred gel is thus impregnated with polyclonal anti-HA antibody. Goat or, more preferably, sheep antisera may be used.

The gel in a SRID assay is preferably an agar or agarose gel, although other suitable materials are available and can be selected by the skilled person based on their ability to support radial diffusion of antigens, and on their ability to support precipitation of antigen/antibody complexes.

Temperatures and timings for diffusion in step (c) are well known in the art.

Methods of the invention may comprise the further step of: (d) determining a dimension of a precipitation halo in the gel. It may then comprise the further step of: (e) comparing the dimension measured in step (d) with a standard dimension, and using the results of the comparison to calculate the antigen concentration in the material applied in step (c). The measurement steps may be performed manually, automatically [11], or semi-automatically. The standard dimension will usually be measured from a sample which contains the antigen of interest at a target concentration. Such concentrations are described in more detail below.

The Starting Composition

The starting composition to be analysed by the SRID assay includes an antigen which is adsorbed to an adjuvant, and this antigen will typically be an influenza virus antigen.

Various forms of influenza virus vaccine are currently available, and are generally based either on live virus or on inactivated virus. The invention can used to analyse inactivated vaccines, which may be based on whole virions, 'split' virions, or on purified surface antigens (including hemagglutinin and, usually, also including neuraminidase). Influenza antigens for analysis can also be presented in the form of virosomes.

Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Virions can be harvested from virus-containing fluids by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents and/or solvents to produce subvirion preparations, including the 'Tween-ether' splitting process. Methods of splitting influenza viruses are well known in the art e.g. see refs. 12-17, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants. Suitable splitting agents include, but are not limited to: ethyl ether, polysorbate 80, deoxycholate, tri-N-butyl phosphate, alkylglycosides, alkylthioglycosides, acyl sugars, sulphobetaines, betaines, polyoxyethylenealkylethers, N,N-dialkyl-Glucamides, Hecameg, alkylphenoxypolyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), nonoxynol 9 (NP9) Sympatens-NP/090,) polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. The BEGRIVAC™, FLUARIX™, FLUZONE™ and FLUSHIELD™ products are split vaccines.

Purified surface antigen vaccines comprise the influenza surface antigens haemagglutinin and, typically, also neuraminidase. Processes for preparing these proteins in purified form are well known in the art. The FLUVIRIN™, AGRIPPAL™ and INFLUVAC™ products are subunit vaccines.

Another form of inactivated influenza antigen is the virosome [18] (nucleic acid free viral-like liposomal particles). Virosomes can be prepared by solubilization of influenza virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane. The invention can be used to store bulk virosomes, as in the INFLEXAL V™ and INVAVAC™ products.

The influenza virus may be attenuated. The influenza virus may be temperature-sensitive. The influenza virus may be cold-adapted. These three features are particularly useful when using live virus as a vaccine antigen.

HA is the main immunogen in current inactivated influenza vaccines, and vaccine doses are standardised by reference to HA levels, typically measured by SRID. Existing vaccines typically contain about 15 μg of HA per strain, although lower doses can be used e.g. for children, or in pandemic situations, or when using an adjuvant. Fractional doses such as ½ (i.e. 7.5 μg HA per strain), ¼ and ⅛ have been used [7,8], as have higher doses (e.g. 3× or 9× doses [19,20]). Thus vaccines analysed according to the invention may include between 0.1 and 150 μg of HA per influenza strain, preferably between 0.1 and 50 μg e.g. 0.1-20 μg, 0.1-15 μg, 0.1-10 μg, 0.1-7.5 μg, 0.5-5 µg, etc. Particular doses include e.g. about 15, about 10, about 7.5, about 5, about 3.8, about 1.9, about 1.5, etc. µg per strain.

Strains used with the invention may have a natural HA as found in a wild-type virus, or a modified HA. For instance, it is known to modify HA to remove determinants (e.g. hyperbasic regions around the HA1/HA2 cleavage site) that cause a virus to be highly pathogenic in avian species.

Influenza virus strains used in vaccines change from season to season. In the current inter-pandemic period, trivalent vaccines include two influenza A strains (H1N1 and H3N2) and one influenza B strain. The invention can be used to analyse both influenza A and influenza B viruses. The invention may be used to analyse monovalent antigen bulks i.e. compositions containing antigen from only a single influenza virus strain. Once analysed, these adsorbed monovalent bulks can then be combined to form multivalent vaccines. The invention may also be used to analyse combined bulks and combined final vaccines.

Influenza A virus currently displays sixteen HA subtypes: H1, H2, H3, H4, H5, H6, H7, H8, H9, H10, H11, H12, H13, H14, H15 and H16. Any of these subtypes can be analysed with the invention. The virus may have any of NA subtypes N1, N2, N3, N4, N5, N6, N7, N8 or N9.

The invention can be used with pandemic influenza A virus strains. Characteristics of a pandemic strain are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the vaccine recipient and the general human population are immunologically naïve to the strain's hemagglutinin; (b) it is capable of being transmitted horizontally in the human population; and (c) it is pathogenic to humans. Pandemic strains H2, H5, H7 or H9 subtype strains e.g. H5N1, H5N3, H9N2, H2N2, H7N1 and H7N7 strains. Within the H5 subtype, a virus may fall into a number of clades e.g. clade 1 or clade 2. Six sub-clades of clade 2 have been identified with sub-clades 1, 2 and 3 having a distinct geographic distribution and are particularly relevant due to their implication in human infections.

Influenza B virus currently does not display different HA subtypes, but influenza B virus strains do fall into two distinct lineages. These lineages emerged in the late 1980s and have HAs which can be antigenically and/or genetically distinguished from each other [21].

Influenza virus antigens analysed according to the invention may have been grown on eggs or on cell culture. The current standard method for influenza virus growth uses specific pathogen-free (SPF) embryonated hen eggs, with virus being purified from the egg allantoic fluid. If the antigen was grown on eggs then the material being analysed may include egg proteins (such as ovalbumin and ovomucoid).

The antigens may have been grown on a cell line that supports influenza virus replication. The cell line will typically be of mammalian origin. Suitable mammalian cells of origin include, but are not limited to, hamster, cattle, primate (including humans and monkeys) and dog cells, although the use of primate cells is not preferred. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line. Suitable dog cells are e.g. kidney cells, as in the CLDK and MDCK cell lines.

Thus suitable cell lines include, but are not limited to: MDCK; CHO; CLDK; HKCC; 293T; BHK; Vero; MRC-5; PER.C6; FRhL2; WI-38; etc. Suitable cell lines are widely available e.g. from the American Type Cell Culture (ATCC) collection [22], from the Coriell Cell Repositories [23], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940.

The most preferred cell lines are those with mammalian-type glycosylation. As a less-preferred alternative to mammalian cell lines, virus can be grown on avian cell lines [e.g. refs. 24-26], including cell lines derived from ducks (e.g. duck retina) or hens e.g. chicken embryo fibroblasts (CEF), etc.

The most preferred cell lines for growing influenza viruses are MDCK cell lines [27-30], derived from Madin Darby canine kidney. The original MDCK cell line is available from the ATCC as CCL-34, but derivatives of this cell line may also be used. For instance, reference 27 discloses a MDCK cell line that was adapted for growth in suspension culture ('MDCK 33016', deposited as DSM ACC 2219). Similarly, reference 31 discloses a MDCK-derived cell line that grows in suspension in serum-free culture ('B-702', deposited as FERM BP-7449). Reference 32 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 33 discloses MDCK cell lines with high susceptibility to infection, including 'MDCK.5F1' cells (ATCC CRL-12042). Compositions containing antigens from viruses grown on any of these MDCK cell lines can be analysed.

Virus may be grown on cells in adherent culture or in suspension. Microcarrier cultures can also be used. In some embodiments, the cells may thus be adapted for growth in suspension.

Cell lines are preferably grown in serum-free culture media and/or protein free media. A medium is referred to as a serum-free medium in the context of the present invention in which there are no additives from serum of human or animal origin. The cells growing in such cultures naturally contain proteins themselves, but a protein-free medium is understood to mean one in which multiplication of the cells occurs with exclusion of proteins, growth factors, other protein additives and non-serum proteins, but can optionally include proteins such as trypsin or other proteases that may be necessary for viral growth.

In addition to antigen and adjuvant, compositions to be analysed may include other pharmaceutical ingredients. A thorough discussion of such components is available in reference 34.

The composition may include preservatives such as thiomersal or 2-phenoxyethanol. It is preferred, however, that the composition should be substantially free from (i.e. less than 5 µg/ml) mercurial material e.g. thiomersal-free [16,35]. Vaccines containing no mercury are more preferred. Preservative-free vaccines are particularly preferred. α-tocopherol succinate can be included as an alternative to mercurial compounds [16].

The composition may include a physiological salt, such as a sodium salt. Sodium chloride (NaCl) is preferred, which may be present at between 1 and 20 mg/ml. Other salts that may be present include potassium chloride, potassium dihydrogen phosphate, disodium hydrogen phosphate dehydrate, sodium dhihydrogen phosphate, dipotassium hydrogen phosphate, magnesium chloride, calcium chloride, etc.

Compositions may have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 6.5 and 8.0, or between 7.0 and 7.8. A process of the invention may therefore include a step of adjusting the pH of the bulk vaccine prior to packaging.

The composition is preferably sterile. The composition is preferably non-pyrogenic e.g. containing <1 EU (endotoxin unit, a standard measure) per dose, and preferably <0.1 EU per dose. The composition is preferably gluten free.

Compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a nonoxynol (NP9), a cetyl trimethyl ammonium bromide ('CTAB'), or sodium deoxycholate, particularly for a split or surface antigen vaccine. The detergent may be present only at trace amounts. Thus the vaccine may included less than 1 mg/ml of each of octoxynol-10 and polysorbate 80. Other residual components in trace amounts could be antibiotics (e.g. neomycin, kanamycin, polymyxin B).

The Adjuvant

Antigen in the sample-to-be-analysed is adsorbed onto an adjuvant. Various adjuvants are able to adsorb antigens, including microparticles and insoluble metal salts e.g. aluminium or calcium salts. Adsorption may be partial or complete. For example, at least 50% of the antigen in a composition (e.g. ≥60%, ≥70%, ≥80%, ≥90%, ≥95%, ≥99%, etc.) may be adsorbed. The degree of adsorption can be determined simply e.g. by centrifuging a composition and determining how much material remains in solution (i.e. is unadsorbed). For example, the adsorption capacity of calcium phosphate adjuvants was measured by this method in reference 36.

The most typical adsorbents for which the methods of the invention will be used are aluminium salts.

Aluminum Salts

Suitable aluminum salts for adsorbing antigens include the adjuvants known as aluminum hydroxide and aluminum phosphate. These names are conventional, but are used for convenience only, as neither is a precise description of the actual chemical compound which is present [e.g. see chapter 9 of reference 37]. The invention can use any of the "hydroxide" or "phosphate" adjuvants that are in general use as adjuvants.

The adjuvants known as "aluminum hydroxide" are typically aluminum oxyhydroxide salts, which are usually at least partially crystalline. Aluminum oxyhydroxide, which can be represented by the formula AlO(OH), can be distinguished from other aluminum compounds, such as aluminum hydroxide Al(OH)$_3$, by infrared (IR) spectroscopy, in particular by the presence of an adsorption band at 1070 cm$^{-1}$ and a strong shoulder at 3090-3100 cm$^{-1}$ [chapter 9 of ref. 37]. The degree of crystallinity of an aluminum hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminum hydroxide adjuvants. The pI of aluminum hydroxide adjuvants is typically about 11 i.e. the adjuvant itself has a positive surface charge at physiological pH. Adsorptive capacities of between 1.8-2.6 mg protein per mg Al$^{+++}$ at pH 7.4 have been reported for aluminum hydroxide adjuvants.

The adjuvants known as "aluminum phosphate" are typically aluminum hydroxyphosphates, often also containing a small amount of sulfate (i.e. aluminum hydroxyphosphate sulfate). They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 1.2. Hydroxyphosphates can be distinguished from strict AlPO$_4$ by the presence of hydroxyl groups. For example, an IR spectrum band at 3164 cm$^{-1}$ (e.g. when heated to 200° C.) indicates the presence of structural hydroxyls [chapter 9 of ref. 37].

The PO$_4$/Al$^{3+}$ molar ratio of an aluminum phosphate adjuvant will generally be between 0.3 and 1.2, preferably between 0.8 and 1.2, and more preferably 0.95±0.1. The aluminum phosphate will generally be amorphous, particularly for hydroxyphosphate salts. A typical adjuvant is amorphous aluminum hydroxyphosphate with PO$_4$/Al molar ratio between 0.84 and 0.92, included at 0.6 mg Al$^{3+}$/ml. The aluminum phosphate will generally be particulate (e.g. plate-like morphology as seen in transmission electron micrographs). Typical diameters of the particles are in the range 0.5-20 µm (e.g. about 5-10 µm) after any antigen adsorption. Adsorptive capacities of between 0.7-1.5 mg protein per mg Al$^{+++}$ at pH 7.4 have been reported for aluminum phosphate adjuvants.

The point of zero charge (PZC) of aluminum phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminum phosphates used according to the invention will generally have a PZC of between 4.0 and 7.0, more preferably between 5.0 and 6.5 e.g. about 5.7.

Suspensions of aluminum salts used with the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The adjuvant includes a mixture of both an aluminum hydroxide and an aluminum phosphate [7]. In this case there may be more aluminum phosphate than hydroxide e.g. a weight ratio of at least 2:1 e.g. ≥5:1, ≥6:1, ≥7:1, ≥8:1, ≥9:1, etc.

The concentration of Al$^{+++}$ in a composition for analysis will usually be <10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml.

As well as including one or more aluminium salt adjuvants, the adjuvant component may include one or more further adjuvant or immunostimulating agents. Such additional components include, but are not limited to: a 3-O-deacylated monophosphoryl lipid A adjuvant ('3d-MPL'); and/or an oilin-water emulsion. 3d-MPL has previously been combined with both aluminum phosphate [38] and aluminum hydroxide [39] adjuvants.

Calcium Salts

Of the various calcium salts, in general only calcium phosphate is used as an adjuvant. Various adjuvant forms of calcium phosphate have been reported, and any of these can be analysed with the methods of the invention.

Hydrated calcium phosphate gel adjuvant is available from Superfos (Vedbaek, Denmark).

Chapter 8 of reference 37 reviewed calcium phosphate adjuvants in 1995. Antigens can be adsorbed to calcium phosphate either by in situ precipitation of the salt in the presence of the antigens or by adsorption to a pre-formed salt. Commercial sources of pre-formed calcium phosphate gel are mentioned. Details are given on the effect of precipitation conditions on physicochemical characteristics of the adjuvant, including adsorption capacity.

Reference 40 reports on the structure and adsorption properties of various calcium phosphate adjuvants. Rather than being strict $Ca_3(PO_4)_2$, the adjuvants were reported to be non-stoichiometric hydroxyapatite of formula $Ca_{10-x}(HPO_4)_x(PO_4)_{6-x}(OH)_{2-x}$ and a pH-dependent surface charge with a point of zero charge (PZC) of 5.5. The adjuvants can form needle-like particles having dimensions of approximately 10 nm×150 nm as well as irregularly shaped plates having diameters of approximately 20-30 nm.

Reference 41 discloses a reactive amorphous calcium phosphate, containing reactive vacant sites, the reactive sites having been obtained by removal of a carbonate pre-component of carbonated amorphous calcium phosphate by thermal decomposition of the pre-component into gaseous or vaporous by-products.

References 42 & 43 disclose a particulate calcium phosphate adjuvant ("CAP"), wherein the particle has a diameter in the range of 300-4000 nm (nanoparticle) and has a spherical shape and a smooth surface. Reference 44 discloses that these particles can be used for mucosal immunization.

Ref. 45 used particulate hydroxylated calcium phosphate of a size suitable for transport across epithelia.

Reference 46 disclosed composite particles that are soluble in vivo and which comprise a particle of a polymeric substance having a calcium phosphate compound having a Ca/P ratio of about 1.0 to 2.0 coated on its surface.

Reference 47 disclosed an injectable aqueous gel of calcium phosphate for adsorbing vaccines, wherein calcium and phosphate ions are combined in proportions such that the weight ratio Ca/P is from 1.62 to 1.85, and such that the settling time of the gel when containing 0.07 atom Ca per liter is between 1-20 mm in 10 minutes at 20° C.

The Ca to P molar ratio of calcium phosphate adjuvants can vary e.g. between 1.35 and 1.83 [see chapter 8 of ref. 37]. The adsorption properties of the adjuvant have been found to vary depending on the conditions used during precipitation e.g. slow mixing gave an adjuvant with lower adsorption capacity that an adjuvant formed by quick mixing.

The amount of calcium phosphate in a vaccine of the invention, measured as $Ca^{++}$, may be between 0.1 and 10 mg/ml e.g. between 0.5-5 mg/ml, preferably 0.75-3 mg/ml, 0.9-1.5 mg/ml, or about 1 mg/ml.

Desorption

The methods of the invention involve desorption of an adsorbed antigen. Various methods can be used for the desorption. For influenza virus antigens, the inventors have found that the nature of the interaction between the surface glycoproteins and aluminium salts (in particular, aluminium hydroxide adjuvant) means that many available desorption methods are either too mild (which means that a proportion of the protein remains bound, leading to an under-estimate of antigen content) or too harsh (meaning that the HA antigen is denatured or cleaved, again leading to an under-estimate of antigen content). Thus the inventors devised desorption treatments that allow substantially complete desorption of influenza proteins while still ensuring that they are assayable by SRID.

Desorption will usually involve mixing the composition-to-be-analysed with a one or more desorption reagents. Suitable desorption reagents include salts and/or surfactants. The desorption reagents may be used at a variety of pH values, but preferably between 6 and 9.5. Desorption may take place at refrigerated temperatures (e.g. between 2-8° C.) or at warmer temperatures (e.g. between 18-25° C.).

Suitable salts for use as desorption reagents include phosphate salts e.g. ammonium phosphate, tri-potassium phosphate, di-potassium phosphate, sodium phosphate, disodium phosphate, etc. These salts can be used at various concentrations e.g. between 10-1000 mM, between 50-500 mM. A concentration of >250 mM (e.g. ≥350 mM, ≥400 mM, ≥450 mM, ≥500 mM, etc.) has been found to give good results e.g. between 300-350 mM, or about 332.5 mM. Thus a desorption salt should remain soluble at this concentration. Other suitable salts may include citrates, carbonates, etc.

Di-potassium hydrogen orthophosphate is a preferred desorption reagent.

Suitable surfactants for use as desorption reagents may be ionic or non-ionic, including zwitterionic. Non-ionic surfactants are particularly useful, and zwitterionic surfactants are preferred. The amphoteric 'Zwittergent' surfactants have been tested, including 'Zwittergent 3-14'™ (n-Tetradecyl-N,N-dimethyl-3-ammonio-1-propanesulfonate; CAS 14933-09-6; 'TDAPS'). Zwittergent 3-14™ is a synthetic water-soluble zwitterionic surfactant that, unlike other amphoteric surfactants, retains its zwitterionic character over a wide pH range. This property is attributed to the presence of both a strongly basic quaternary ammonium ion and an acidic sulfonate ion of equal strength. Thus preferred surfactants include a quaternary ammonium ion and/or an acidic sulfonate ion. Surfactants can be used at various concentrations e.g. from 0.1-15%, from 1-10%, etc. Zwittergent 3-14™ is useful at a concentration range between 0.1% to 2% e.g. 0.25% to 1%, or at about 0.5%.

Preferred desorption uses a mixture of a salt and a surfactant.

Further Methods

The invention provides a method for producing a vaccine, comprising the steps of:
(i) preparing a bulk antigen of interest;
(ii) analyzing a sample of the bulk antigen using the methods of the invention;
(iii) based on the results of step (ii), diluting the bulk antigen to a desired final concentration;
(iv) optionally combining the diluted bulk antigen with one or more pharmaceutically acceptable ingredients; and
(v) packaging the diluted bulk antigen for distribution.

The bulk antigen of step (i) may be monovalent or multivalent. The ingredients in step (iv) may include carriers, excipients, further antigens, etc.

The invention also provides a method for preparing a sample for analysis by a SRID assay, comprising the steps of (a) obtaining a starting composition comprising an antigen of interest, wherein the antigen is adsorbed to an adjuvant; and (b) treating the starting composition to desorb the antigen from the adjuvant. The product of step (b) may then be analysed by a SRID assay. The preparative method and the actual SRID assay may be performed by the same person or a different person, and may be performed in the same geographical location or in different geographical locations e.g. in different countries.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

The A/New York H3N2 influenza surface glycoproteins and the aluminium hydroxide adjuvant were mixed thoroughly by vortexing and incubated at ambient temperature for 18 hours (+/−3 hours). The formulations were then centrifuged at 16,250 g for 4 minutes to pellet the aluminium hydroxide together with adsorbed antigen. Pelleted adsorbed antigen was resuspended in a variety of desorption solutions made of these components and then incubated at ambient temperature for at least 18 hours (+/−3 hours). The formulations were then centrifuged at 16,250 g for 4 minutes to pellet the aluminium hydroxide. Desorbed antigen in the supernatant was measured by protein assay, and results were expressed as a % of the total protein present. Recoveries of less than 0% or more than 100% were possible because of experimental error and variation in the accuracy of the procedures used.

Results were as follows, with the two columns showing % desorbed protein recovery (left) and the final phosphate concentration (mM) in solution (right):

| Buffer | mM | pH | Zwittergent | | | | | | | |
|---|---|---|---|---|---|---|---|---|---|---|
| | | | 0% | | 6% | | 7% | | 8% | |
| Ammonium phosphate | 50 | 8.1 | 6% | 50 | 35% | 25 | 19% | 28 | 40% | 31 |
| | 100 | 8.1 | 27% | 100 | 65% | 50 | 66% | 56 | 66% | 63 |
| | 250 | 8.1 | 35% | 250 | 70% | 125 | 77% | 141 | 79% | 156 |
| | 350 | 8.2 | 28% | 350 | 73% | 175 | 73% | 197 | 65% | 219 |
| | 500 | 8.2 | 35% | 500 | 76% | 250 | 78% | 281 | 71% | 313 |
| Potassium phosphate (tri-basic) | 50 | 12.2 | 75% | 50 | 92% | 5 | >100% | 28 | 99% | 31 |
| | 100 | 13.4 | 64% | 100 | >100% | 50 | >100% | 56 | >100% | 63 |
| | 250 | 12.6 | 56% | 250 | 68% | 125 | 92% | 141 | 75% | 156 |
| | 350 | 12.7 | 33% | 350 | 82% | 175 | 93% | 197 | 82% | 219 |
| | 500 | 12.8 | 14% | 500 | >100% | 250 | 95% | 281 | 97% | 313 |
| Disodium hydrogen orthophosphate | 50 | 9.1 | 0% | 50 | 27% | 5 | 18% | 28 | 19% | 31 |
| | 100 | 9.2 | 0% | 100 | 55% | 50 | 55% | 56 | 63% | 63 |
| | 250 | 9.1 | 0% | 250 | 75% | 125 | 74% | 141 | 81% | 156 |
| | 350 | 9.1 | 0% | 350 | 96% | 175 | 79% | 197 | >100% | 219 |
| | 500 | 9.1 | 0% | 500 | >100% | 250 | >100% | 281 | 100% | 313 |
| Di-potassium hydrogen orthophosphate | 50 | 9.2 | 0% | 50 | 23% | 5 | 19% | 28 | 16% | 31 |
| | 100 | 9.2 | 8% | 100 | 45% | 50 | 41% | 56 | 59% | 63 |
| | 250 | 9.3 | 0% | 250 | 67% | 125 | 54% | 141 | 61% | 156 |
| | 350 | 9.3 | 0% | 350 | >100% | 175 | 73% | 197 | 85% | 219 |
| | 500 | 9.3 | 10% | 500 | >100% | 250 | >100% | 281 | 100% | 313 |
| Di-sodium hydrogen orthophosphate | 50 | 9.1 | 0% | 50 | 54% | 5 | 18% | 28 | 21% | 31 |
| | 100 | 9.2 | 13% | 100 | 56% | 50 | 55% | 56 | 68% | 63 |
| | 250 | 9.1 | 35% | 250 | 71% | 125 | 73% | 141 | 94% | 156 |
| | 350 | 9.1 | 61% | 350 | 95% | 175 | 83% | 197 | 97% | 219 |
| | 500 | 9.1 | 73% | 500 | 99% | 250 | >100% | 281 | >100% | 313 |

MODES FOR CARRYING OUT THE INVENTION

Evaluation of Various Salts

Bulk monovalent surface glycoproteins were prepared from egg-grown A/New York (H3N2) influenza virus. The antigen (50 µg/ml) was fully adsorbed to an aluminium hydroxide adjuvant (1 mg/ml Alhydrogel™), after which it could no longer be reliably analysed by SRID. Thus various desorption reagents were tested (final concentrations given in table below):

Buffer salts: ammonium phosphate
potassium phosphate (tri-basic)
di-potassium hydrogen orthophosphate
sodium dihydrogen phosphate
disodium hydrogen orthophosphate
Surfactant Zwittergent 3-14™

Ammonium phosphate was not tested further, as it was incompatible with the BCA protein assay and gave low protein recoveries.

Thus full antigen recovery could be readily achieved using a mixture of surfactant and phosphate salts. A high salt concentration (≥350 mM) tended to give the best results. The best results were achieved with di-potassium hydrogen orthophosphate. This salt could be readily dissolved at high concentrations (e.g. 0.5M) while consistently achieving HA desorption at a pH which maintains the protein's native conformation (less than 9.5).

Salt and Detergent Concentration Ranges

Monovalent surface glycoproteins were prepared from egg-grown A/Vietnam/1203/2004 (H5N1) reassortant. The surface antigen (HA concentration 90 µg/ml) was fully adsorbed to aluminium hydroxide in a ratio of 60 µg haemagglutinin per mg aluminium hydroxide. The formulation was vortexed thoroughly and stored until use at 4° C.

To assess desorption under a range of potassium phosphate and Zwittergent 3-14™ concentrations, aliquots of the formulation were vortexed and then centrifuged at 13,000 rpm for 5 minutes to pellet the aluminium hydroxide together with adsorbed antigen. A range of alternative desorption solutions were evaluated:

(1) 300 mM dipotassium hydrogen phosphate plus 0.5% (w/v) Zwittergent 3-14™
(2) 350 mM dipotassium hydrogen phosphate plus 0.5% (w/v) Zwittergent 3-14™
(3) 400 mM dipotassium hydrogen phosphate plus 0.5% (w/v) Zwittergent 3-14™
(4) 300 mM dipotassium hydrogen phosphate plus 1.0% (w/v) Zwittergent 3-14™
(5) 350 mM dipotassium hydrogen phosphate plus 1.0% (w/v) Zwittergent 3-14™
(6) 400 mM dipotassium hydrogen phosphate plus 1.0% (w/v) Zwittergent 3-14™
(7) 300 mM dipotassium hydrogen phosphate plus 2.0% (w/v) Zwittergent 3-14™
(8) 350 mM dipotassium hydrogen phosphate plus 2.0% (w/v) Zwittergent 3-14™
(9) 400 mM dipotassium hydrogen phosphate plus 2.0% (w/v) Zwittergent 3-14™

The desorption buffer was added to the pellet, resuspended through vortexing and incubated at 4° C. overnight. Each sample was then centrifuged at 13,000 rpm for 5 minutes and the supernatant was assayed for protein content.

The quantities of protein that were desorbed and assayed in the supernatant were as follows (μg/ml):

|  | Dipotassium hydrogen phosphate concentration (mM) | | |
|---|---|---|---|
| % Zwittergent ™ | 350 | 400 | 450 |
| 0.5 | 101.8 | 97.8 | 95.4 |
| 1.0 | 104.4 | 93.9 | 95.4 |
| 2.0 | 76.8 | 80.1 | 66.4 |

Thus, with a 90 μg antigen dose and this aluminium hydroxide adjuvant, desorption is optimum at dipotassium hydrogen phosphate concentrations of 350-450 mM in combination with Zwittergent 3-14™ concentrations between 0.5-1.0% (w/v).

Evaluation of Alternative Hemagglutinin Concentrations (Part 1)

Based on the results with A/New York (H3N2), antigen from pandemic strain A/Vietnam/1203/2004 (H5N1) was prepared and adsorbed to aluminium hydroxide as described above. HA concentrations of 90, 60, 30, 15 and 7.5 μg/ml were used. The ratio of HA to aluminium hydroxide was kept at 30 μg HA for 1 mg aluminium hydroxide. Mixtures of $K_2HPO_4.3H_2O$ (350, 500 and 750 mM) and Zwittergent 3-14™ (0.5%, 2% or 4%) were used for desorption. The final buffer concentrations after Zwittergent addition were:

| Phosphate Buffer | Molar Conc" (mM) | Zwittergent 3-14 (%) | Final Buffer Conc" (mM) |
|---|---|---|---|
| $K_2HPO_4$ | 350 | 0.5 | 332.5 |
| | | 2 | 280 |
| | | 4 | 210 |
| | 500 | 0.5 | 475 |
| | | 2 | 400 |
| | | 4 | 300 |
| | 750 | 0.5 | 712.5 |
| | | 2 | 600 |
| | | 4 | 450 |

Desorption was performed according to the conditions described above, except that the incubation temperature for the desorption step was 2-8° C.

SRID hemagglutinin recoveries were as follows:

| $K_2HPO_4 \cdot 3H_2O$ | | Zwittergent | | |
|---|---|---|---|---|
| (starting concentration) | HA | 0.5% | 2% | 4% |
| 350 mM | 7.5 | 136 | 88 | 52 |
| | 15 | 91 | 60 | 69 |
| | 30 | 82 | 71 | 50 |
| | 60 | 101 | 53 | 45 |
| | 90 | 90 | 75 | 62 |
| 500 mM | 7.5 | 117 | 92 | 60 |
| | 15 | 76 | 55 | 63 |
| | 30 | 69 | 58 | 44 |
| | 60 | 95 | 45 | 40 |
| | 90 | 87 | 55 | 47 |
| 750 mM | 7.5 | 99 | 83 | 72 |
| | 15 | 75 | 65 | 47 |
| | 30 | 79 | 56 | 56 |
| | 60 | 81 | 48 | 48 |
| | 90 | 74 | 59 | 60 |

This study indicates that the optimal combination of Zwittergent 3-14™ for this antigen and adjuvant is 0.5%, with 332.5 mM (final concentration) dipotassium hydrogen phosphate.

Evaluation of Alternative Hemagglutinin Concentrations (Part 2)

Antigen from pandemic strain A/Vietnam/1203/2004 (H5N1) was prepared and adsorbed to aluminium hydroxide as described above. HA concentrations of 90, 60, 30, 15 and 7.5 μg/ml were used. The ratio of HA to Aluminium hydroxide was kept at 30 μg HA for 1 mg aluminium hydroxide. Mixtures of $K_2HPO_4.3H_2O$ (350 mM) and Zwittergent 3-14™ (0.5%, 2% or 4%) were used for desorption. The final buffer concentrations after Zwittergent addition were: 0.5% Zwittergent=332.5 mM, 2% Zwittergent=280 mM and 4% Zwittergent=210 mM. Desorption was performed according to the conditions described above, except that the incubation temperature for the desorption step was 2-8° C.

Results were as follows (AMT=arithmetic mean titre):

| | | SRID (μgHA/ml) | | | | |
|---|---|---|---|---|---|---|
| A/Vietnam Formulation | Zwittergent Conc (%) | Plate 1 | Plate 2 | Plate 3 | AMT (μgHA/ml) | % Recovery |
| 90 μgHA | 0.5 | 73.47 | 109.48 | 67.75 | 83.9 | 103 |
| | 2 | 65.01 | 63.72 | 68.96 | 65.9 | 81 |
| | 4 | 57.86 | 44.45 | 43.9 | 48.7 | 60 |
| | Non-Adjuvanted | 81.5 | * | * | * | |

-continued

| A/Vietnam Formulation | Zwittergent Conc (%) | SRID (μgHA/ml) | | | AMT (μgHA/ml) | % Recovery |
|---|---|---|---|---|---|---|
| | | Plate 1 | Plate 2 | Plate 3 | | |
| 60 μgHA | 0.5 | 53.15 | 50.4 | 48.48 | 50.7 | 101 |
| | 2 | 48.37 | 42.96 | 42.34 | 44.6 | 89 |
| | 4 | 36.91 | 36.65 | 34.46 | 36.0 | 72 |
| | Non-Adjuvanted | 50.2 | * | * | * | |
| 30 μgHA | 0.5 | 26.97 | 25.90 | 27.84 | 26.9 | 97 |
| | 2 | 29.61 | 21.72 | 23.24 | 24.9 | 90 |
| | 4 | 18.44 | 20.18 | 17.49 | 18.7 | 67 |
| | Non-Adjuvanted | 27.8 | * | * | * | |
| 15 μgHA | 0.5 | 12.79 | 14.12 | 15.84 | 14.2 | 108 |
| | 2 | 9.94 | 7.34 | 10.19 | 9.2 | 70 |
| | 4 | 8.63 | 6.88 | 12.80 | 9.4 | 71 |
| | Non-Adjuvanted | 13.2 | * | * | * | |
| 7.5 μgHA | 0.5 | 9.35 | 6.50 | 6.24 | 7.4 | 97 |
| | 2 | 3.97 | 4.94 | 5.77 | 4.9 | 65 |
| | 4 | 7.63 | 4.75 | 2.60 | 5.0 | 66 |
| | Non-Adjuvanted | 7.6 | * | * | * | |

* One plate was run for the non-adjuvanted sample

Optimal desorption for this antigen and adjuvant was observed for a Zwittergent 3-14™ concentration of 0.5% (final dipotassium hydrogen phosphate concentration of 332.5 mM). Higher concentrations of Zwittergent resulted in an apparent reduced recovery of hemagglutinin. Taken together with the results of the previous investigations, this is probably due to the reduced concentration of the dipotassium hydrogen phosphate used at the higher detergent concentration. Thus 0.5% Zwittergent 3-14 in combination with 332.5 mM dipotassium hydrogen phosphate is the preferred combination to ensure desorption of a range of hemagglutinin concentrations from aluminium hydroxide adjuvant.

Confirmation of Procedure Robustness

To assess the robustness of the assay, a second operator was used to perform a parallel run using equivalent samples.

A/Vietnam/1203/2004 purified surface glycoproteins were formulated to 30, 15 and 7.5 μg HA/ml with 3 mg/ml aluminium hydroxide. After overnight incubation at 2-8° C., the formulated material was centrifuged at 16,250 g for 5 minutes to pellet the adjuvant and approximately 900 µl of the supernatant was removed carefully so that the pellet was not disturbed. These supernatants were analysed for haemagglutinin by SRID and total protein using the Pierce BCA protein assay to prove that all protein had bound to the adjuvant and none remained in solution.

50 µl of a 10% Zwittergent 3-14 (w/v) solution was added to the pellet together with 950 µl of 350 mM $K_2HPO_4$ desorption buffer making a final concentration of 0.5% Zwittergent 3-14™ and 332.5 mM $K_2HPO_4$, pH 9.4.

The solutions were vortexed thoroughly for a minimum of 10 minutes to resolubilise the pellets and incubated at 4-8° C. for 18±3 hrs.

Following incubation the solutions were vortexed for a minimum of 10 seconds and then centrifuged at 16,250 g for 5 minutes to pellet the adjuvant. The supernatants were carefully removed and analysed for hemagglutinin by SRID.

The data presented in the tables below are the SRID assay data from the parallel run assays.

SRID assay parallel run, Operator 1

| A/Vietnam (µgHA/ml + 3 mg/ml Al-hydroxide | Plate 1 | Plate 2 | Plate 3 | AMT (µgHA/ml) | % Recovery |
|---|---|---|---|---|---|
| 30 | 27.86 | 25.66 | 25.97 | 26.5 | 88 |
| 15 | 12.25 | 11.65 | 14.12 | 12.7 | 85 |
| 7.5 | 9.26 | 5.79 | 5.98 | 7.0 | 93 |

SRID assay parallel run, Operator 2

| A/Vietnam (µgHA/ml + 3 mg/ml Al-hydroxide | Plate 1 | Plate 2 | Plate 3 | AMT (µgHA/ml) | % Recovery |
|---|---|---|---|---|---|
| 30 | 30.23 | 26.55 | 33.66 | 30.1 | 100 |
| 15 | 12.63 | 15.78 | 16.56 | 15.0 | 100 |
| 7.5 | 8.32 | 5.31 | 7.24 | 7.0 | 93 |

These results demonstrate that there was good intermediate precision between both operators.

It will be understood that the invention has been described by way of example only and modifications may be made whilst remaining within the scope and spirit of the invention.

REFERENCES

[1] *Vaccines*. (eds. Plotkin & Orenstein). 4th edition, 2004, ISBN: 0-7216-9688-0.
[2] U.S. Pat. No. 6,372,223.
[3] WO00/15251.
[4] Govorkova et al. (2006) *J Infect Dis.* 194(2):159-67.
[5] Bresson et al. (2006) *Lancet* 367:1657-64.
[6] Lin et al. (2006) *Lancet.* 368:991-7.
[7] WO01/22992.
[8] Hehme et al. (2004) *Virus Res.* 103(1-2):163-71.
[9] Williams (1993) *Vet Microbial* 37:253-262.
[10] Fitzgerald & Needy (1986) *Dev Biol Stand* 64:73-79.
[11] WO2005/033695.
[12] WO02/28422.
[13] WO02/067983.
[14] WO02/074336.
[15] WO01/21151.
[16] WO02/097072.
[17] WO2005/113756.
[18] Huckriede et al. (2003) *Methods Enzymol* 373:74-91.
[19] Treanor et al. (1996) *J Infect Dis* 173:1467-70.
[20] Keitel et al. (1996) *Clin Diagn Lab Immunol* 3:507-10.
[21] Rota et al. (1992) *J Gen Virol* 73:2737-42.
[22] http://www.atcc.org/
[23] http://locus.umdnj.edu/
[24] WO03/076601.
[25] WO2005/042728.
[26] WO03/043415.
[27] WO97/37000.
[28] Brands et al. (1999) *Dev Biol Stand* 98:93-100.
[29] Halperin et al. (2002) *Vaccine* 20:1240-7.
[30] Tree et al. (2001) *Vaccine* 19:3444-50.
[31] EP-A-1260581 (WO01/64846).
[32] WO2006/071563.
[33] WO2005/113758.

[34] Gennaro (2000) *Remington: The Science and Practice of Pharmacy.* 20th edition, ISBN: 0683306472.
[35] Banzhoff (2000) *Immunology Letters* 71:91-96.
[36] Aggerbeck & Heron (1995) *Vaccine* 13:1360-5.
[37] *Vaccine Design: The Subunit and Adjuvant Approach* (ed. Powell & Newman) 1995 (ISBN 0-306-44867-X).
[38] WO96/26741.
[39] WO93/19780.
[40] Jiang et al. (2004) *Vaccine* 23:693-8.
[41] U.S. Pat. No. 5,676,976.
[42] WO00/46147.
[43] U.S. Pat. No. 6,355,271.
[44] WO03/051394.
[45] U.S. Pat. No. 5,443,832.
[46] U.S. Pat. No. 5,851,670.
[47] U.S. Pat. No. 4,016,252.

The invention claimed is:

1. A method for producing a vaccine, comprising the steps of: (i) preparing a bulk antigen of interest; (ii) analyzing a sample of the bulk antigen by performing an immunodiffusion assay, comprising the steps of: (a) obtaining a starting composition comprising an influenza virus hemagglutinin (HA) antigen of interest, wherein the HA antigen is adsorbed to an adjuvant that comprises an aluminium salt; (b) treating the starting composition to desorb the HA antigen from the adjuvant; (c) centrifuging a desorbed composition of (b); and (d) allowing supernatant from the centrifuged desorbed composition, or a sample thereof, to diffuse into a gel that contains antibody specific to the HA antigen of interest; and, based on the results of step (ii), (iii) diluting the bulk antigen to a desired final concentration; optionally (iv) combining the diluted bulk antigen with one or more pharmaceutically acceptable ingredients; and (v) packaging the diluted bulk antigen for distribution.

2. The method of claim 1, wherein antigen is desorbed in step (b) by mixing the starting composition, or a sample thereof, with a desorption reagent comprising a salt.

3. The method of claim 2, wherein the salt is a phosphate salt.

4. The method of claim 3, wherein the salt is an ammonium phosphate, a potassium phosphate, or a sodium phosphate, disodium phosphate.

5. The method of claim 4, wherein the salt is a di-potassium hydrogen orthophosphate.

6. The method of claim 1, wherein antigen is desorbed in step (b) by mixing the starting composition, or a sample thereof, with a desorption reagent comprising a surfactant.

7. The method of claim 6, wherein the desorption reagent comprises a zwitterionic surfactant.

8. The method of claim 7, wherein the surfactant is n-Tetradecyl-N,N-dimethyl-3-ammonio-1-propanesulfonate.

9. The method of claim 1, wherein antigen is desorbed in step (b) using a desorption reagent comprising dipotassium hydrogen orthophosphate and n-Tetradecyl-N,N-dimethyl-3-ammonio-1-propanesulfonate.

10. The method of claim 9, wherein the desorption reagent has 300-350 mM dipotassium hydrogen orthophosphate and 0.5% n-Tetradecyl-N,N-dimethyl-3-ammonio-1-propanesulfonate.

11. The method of claim 1, wherein step (d) involves diffusion from a well in a gel, and wherein, between steps (c) and (d), the method includes a step in which a desorbed composition, or a sample thereof, is introduced into the well.

12. The method of claim 1, wherein the gel used in step (d) is an agar gel or an agarose gel.

13. The method of claim 1, comprising the further step of: (e) determining a dimension of a precipitation halo in the gel.

14. The method of claim 13, comprising the further step of: (f) comparing the dimension measured in step (e) with a standard dimension, and using the results of the comparison to calculate the antigen concentration in the material applied in step (d).

15. The method of claim 1, wherein the starting composition is an inactivated influenza vaccine.

16. The method of claim 15, wherein the vaccine includes whole virions.

17. The method of claim 15, wherein the vaccine includes split virions.

18. The method of claim 15, wherein the vaccine includes virosomes.

19. The method of claim 15, wherein the vaccine includes purified surface antigens.

20. The method of claim 1, wherein the adjuvant comprises an aluminium phosphate.

21. The method of claim 1, wherein the adjuvant comprises an aluminium hydroxide.

22. The method of claim 21, wherein the adjuvant comprises a mixture of an aluminium hydroxide and an aluminium phosphate.

* * * * *